United States Patent
Salam et al.

(10) Patent No.: US 10,456,073 B2
(45) Date of Patent: Oct. 29, 2019

(54) SYSTEM, METHOD AND APPARATUS FOR RAPID BRIEF FEEDBACK INTRACEREBRAL STIMULATION BASED ON REAL-TIME DESYNCHRONIZATION

(71) Applicants: THE GOVERNING COUNCIL OF THE UNIVERSITY OF TORONTO, Toronto (CA); THE HOSPITAL FOR SICK CHILDREN, Toronto (CA)

(72) Inventors: Muhammad Tariqus Salam, Toronto (CA); Roman Genov, Toronto (CA); Jose Luis Perez-Velazquez, Toronto (CA)

(73) Assignees: THE GOVERNING COUNCIL OF THE UNIVERSITY OF TORONTO, Toronto (CA); THE HOSPITAL FOR SICK CHILDREN, Toronto (CA)

(*) Notice: Subject to any disclaimer, the term of this patent is extended or adjusted under 35 U.S.C. 154(b) by 0 days.

(21) Appl. No.: 15/177,615

(22) Filed: Jun. 9, 2016

(65) Prior Publication Data

US 2016/0361546 A1     Dec. 15, 2016

Related U.S. Application Data

(60) Provisional application No. 62/172,912, filed on Jun. 9, 2015.

(51) Int. Cl.
| | |
|---|---|
| *A61N 1/36* | (2006.01) |
| *A61B 5/00* | (2006.01) |
| *A61B 5/0478* | (2006.01) |
| *A61B 5/04* | (2006.01) |

(52) U.S. Cl.
CPC ........ *A61B 5/4094* (2013.01); *A61B 5/04012* (2013.01); *A61B 5/0478* (2013.01); *A61B 5/4836* (2013.01); *A61B 5/6868* (2013.01); *A61N 1/36064* (2013.01)

(58) Field of Classification Search
CPC .................................................. A61B 5/0478
See application file for complete search history.

(56) References Cited

U.S. PATENT DOCUMENTS

| | | | |
|---|---|---|---|
| 6,597,954 B1 * | 7/2003 | Pless .................... | A61B 5/0476 600/544 |
| 7,212,110 B1 | 5/2007 | Martin et al. | |
| 8,180,452 B2 | 5/2012 | Shaquer | |

(Continued)

FOREIGN PATENT DOCUMENTS

| | | |
|---|---|---|
| CN | 102157989 A | 8/2011 |
| WO | 2015092747 A2 | 6/2015 |

OTHER PUBLICATIONS

Schindler et al., "Increasing synchronization may promote seizure termination: Evidence from status epilepticus", Jun. 18, 2007, Clinical Neurophysiology, 118, 1955-1968.*

(Continued)

*Primary Examiner* — Carl H Layno
*Assistant Examiner* — Jennifer L Ghand
(74) *Attorney, Agent, or Firm* — Marc Lampert; Anil Bhole; Bhole IP Law

(57) ABSTRACT

There is provided a system, methods and apparatuses for stopping the development of paroxysms based on a feedback stimulation at low frequencies for a few seconds after the detection of a seizure precursor.

9 Claims, 8 Drawing Sheets

(56) References Cited

U.S. PATENT DOCUMENTS

| | | | |
|---|---|---|---|
| 9,030,239 B1 | 5/2015 | Dastgheib et al. | |
| 2004/0068199 A1* | 4/2004 | Echauz | A61B 5/0476 600/544 |
| 2007/0067003 A1* | 3/2007 | Sanchez | A61N 1/36082 607/45 |
| 2007/0150024 A1* | 6/2007 | Leyde | A61B 5/0476 607/45 |
| 2007/0213786 A1* | 9/2007 | Sackellares | A61B 5/0476 607/45 |
| 2008/0176271 A1 | 7/2008 | Silver et al. | |
| 2010/0197524 A1 | 8/2010 | Janata et al. | |
| 2011/0130797 A1* | 6/2011 | Talathi | A61B 5/0476 607/3 |
| 2012/0078071 A1 | 3/2012 | Bohm et al. | |
| 2012/0283800 A1 | 5/2012 | Perryman et al. | |
| 2013/0172774 A1* | 7/2013 | Crowder | A61B 5/04 600/544 |
| 2014/0012122 A1 | 1/2014 | Sadek et al. | |

OTHER PUBLICATIONS

Written Opinion of the International Searching Authority corresponding to PCT/CA2016/051169; Canadian Intellectual Property Office; dated Jan. 13, 2017.
International Search Report corresponding to PCT/CA2016/051169; Canadian Intellectual Property Office; dated Jan. 13, 2017.
Bagheri, A., et al. (2013) Massively-Parallel Neuromonitoring and Neurostimulation Rodent Headset With Islanotextured Flexible Microelectrodes. IEEE Transactions on Biomedical Circuits and Systems, 7:601-609.
Medeiros, D.D., Moraes M.F. (2014) Focus on Desynchronization Rather Than Excitability: A New Strategy for Intraencephalic Electrical Stimulation. Epilepsy Behav, 38C:32-36.
Jiruska, P., et al. (2010) Effects of Direct Brain Stimulation Depend on Seizure Dynamics. Epilepsia 51:93-97.
Lockman, J., Fisher, R.S. (2009) Therapeutic Brain Stimulation for Epilepsy. Neurologic Clinics 27:1031-1040.
Sun, F.T., Morrell, M.J. (2014) The RNS System: Responsive Cortical Stimulation for the Treatment of Refractory Partial Epilepsy. Expert Review of Medical Devices, 11:563-572.
Krook-Magnuson, E., et al. (2013) On-Demand Optogenetic Control of Spontaneous Seizures in Temporal Lobe Epilepsy. Nature Communications, 4:1376.
Weiss, S.R., et al., (1995) Quenching: Inhibition of Development and Expression of Amygdala Kindled Seizures With Low Frequency Stimulation. Neuroreport, 6:2171-2176.
Tergau, F., et al. (1999) Low-Frequency Repetitive Transcranial Magnetic Stimulation Improves Intractable Epilepsy. Lancet, 353:2209.
Koubeissi, M.Z. et al., (2013) Low-Frequency Electrical Stimulation of a Tiber Tract in Temporal Lobe Epilepsy. Annals of Neurology, 74:223-231.
Colpan, M.E., et al., (2007) Proportional Feedback Stimulation for Seizure Control in Rats. Epilepsia, 48:1594-1603.
Good, L.B. et al., (2009) Control of Synchronization of Brain Dynamics Leads to Control of Epileptic Seizures in Rodents. International Journal of Neural Systems, 19:173-196.
Rashid, S. et al. (2012)Low Frequency Stimulation of Ventral Hippocampal Commissures Reduces Seizures in a Rat Model of Chronic Temporal Lobe Epilepsy. Epilepsia, 53:147-156.
Osorio, I., Frei M.G. (2009) Seizure Abatement With Single DC Pulses: Is Phase Resetting at Play? International Journal of Neural Systems, 19:149-156.
International Search Report corresponding to PCT/CA2016/050655; Canadian Intellectual Property Office; dated Sep. 7, 2016.
Written Opinion of the International Searching Authority corresponding to PCT/CA2016/050655; Canadian Intellectual Property Office; dated Sep. 7, 2016.
"The 128-Channel Fully Differential Digital Integrated Neural Recording and Stimulation Interface" Shahrokhi et al [online], May 24, 2010 (May 24, 2010), [Retrieved on Oct. 12, 2017 (Dec. 10, 2017). Retrieved from: http://ieeexplore.ieee.org/document/5471738/authors?part=1.
"Design of an Optimal & Closed-Loop Neurostimulation System for treatment of Epilepsy" Gao, Richard, [online], Nov. 23, 2015 (Nov. 23, 2015], Retrieved on Oct. 12, 2017 (Dec. 10, 2017). Retrieved from: http:www,undergraduatelibrary.org/2014/medical-sciences/design-optimal-closed-loop-neuromodulation-system-treatment-epilepsy.
"Micropower CMOS Integrated Low-Noise Amplification, Filtering, and Digitization of Multimodal Neuroptentials" Mollazadeh et al. [online], Jan. 1, 2010 (Jan. 1, 2010). Retrieved Oct. 12, 2017 (Dec. 10, 2017). Retrieved from: https://www.ncbi.nlm.nih.gov/pmc/articles/PMC2747318/.
International Search Report corresponding to PCT/2017/050867; Canadian Intellectual Property Office; dated Oct. 18, 2017.
Written Opinion of the International Searching Authority corresponding to PCT/CA2017/050867; Canadian Intellectual Property Office; dated Oct. 18, 2018.
Supplementary Partial European Search Report for EU patent application No. 16806476.4, EPO, dated Feb. 14, 2019.
Panagiotis Kassanos et al: ACMOS Magnitude/Phase Measurement Chip for Impedance Spectroscopy, IEEE Sensors Journal, vol. 13, No. 6, Jun. 2013.
Supplementary Partial European Search Report for EU patent application No. 16852943.6, EPO, dated Apr. 11, 2019.
Kassiri, Hossein et al.: Inductively-powered direct-coupled 64-channel chopper-stabilized epilepsy-responsive neurostimulator with digital offset cancellation and tri-band radio, 2013 Proceedings of the ESSCIRC (ESSCIRC), IEEE, Sep. 22, 2014, pp. 95-98.
Soltani, Nima et al., Cellular inductive powering system for weakly-linked resonant rodent implants, 2013 IEEE Biomedical Circuits and Systems Conference (Biocas), IEEE, Oct. 31, 2013, pp. 350-353.
European Search Opinion for EU patent application No. 16852943.6, EPO, daed Apr. 11, 2019.
Supplementary European Search Report for EU patent application No. 16806476.4, EPO, dated Jun. 18, 2019.
European Search Opinion for EU patent application No. 16806476.4, EPO, dated Jun. 18, 2019.
Panagiotis Kassanos et al: A CMOS magnitude/phase measurement chip for impedance spectroscopy, IEEE Sensors Journal, IEEE Service Center, New York, NY, US, vol. 13, No. 6, Jun. 1, 2013 (Jun. 1, 2013), pp. 2229-2236, XP011506442, ISSN: 1530-437X, DOI: 10.1109/JSEN.2013.2251628.

* cited by examiner

SYSTEM, METHOD AND APPARATUS FOR RAPID BRIEF FEEDBACK INTRACEREBRAL STIMULATION BASED ON REAL-TIME DESYNCHRONIZATION

TECHNICAL FIELD

The following describes, generally, feedback stimulation after the detection of a seizure precursor to stop the development of paroxysms and, more specifically, based on phase desynchronization.

BACKGROUND

Epilepsy is a dynamical disease. Over the past decade, many seizure prediction and detection algorithms have been proposed to anticipate seizures, however detection delays are 5-15 seconds after the seizure onset, which is too late to be used as a signal for perturbations that may abort the paroxysm before it starts. Furthermore, improving the performance of these algorithms by increasing computational power may slow down closed loop monitoring systems and may be not suitable for real-time applications.

SUMMARY

In one aspect, a method of monitoring, detecting and stimulating a human patient with epilepsy is provided, said method comprising: monitoring said patient for a seizure onset by real-time intracranial EEG (icEEG) microelectrodes coupled to two hippocampi of the patient; detecting said seizure onset using phase synchronization analysis; and stimulating a hippocampus (seizure origination) of the patient upon detection of a seizure onset by said sensed icEEG of said hippocampi.

Said monitoring may comprise identifying phase desynchronization at theta wave in between said hippocampi icEEG recordings at seizure onset.

The method may further comprise: amplifying said sensed icEEG of said hippocampi to obtain amplified icEEG recordings; digitalizing said amplified icEEG recording to obtain the digital data; using said digital data and said seizure onset detection algorithm to trigger a current stimulator for said stimulation of said hippocampus.

Phase synchronization analysis may comprise: filtering said amplified icEEG recordings with cutoff frequencies of center frequency±2 Hz; investigating phase synchrony index at said cutoff frequencies, where said phase synchrony index is defined as $R=|\langle e^{i\Delta\theta}\rangle|$, where $\Delta\theta$ is the phase difference between the said hippocampi recordings; and averaging said phase synchrony index values throughout a 1 sec time window.

The central frequency may be one of 5 Hz, 8 Hz, 15 Hz and 25 Hz.

Stimulating said hippocampus may be accomplished with a stimulation parameters: 5-second train of 5 Hz stimulus pulses.

Stimulating with said parameters may restore said theta wave synchronization in between said hippocampi during said phase desynchronization at theta wave at seizure onset.

Stimulating may comprise: implanting two bipolar microelectrodes (each bipolar microelectrode comprises assembling of two insulated microwires and exposed tip of the wire uses for icEEG recoding; diameter of the exposed region: 100 μm and interspacing between two wires: 25 μm) into CA regions of said hippocampi; and passing current stimulation pulses between two contacts of said a bipolar microelectrode through tissue of said hippocampus.

Monitoring said patient for seizure onset by sensing icEEG recordings of said hippocampi may comprise sensing icEEG of said hippocampi with said two bipolar microelectrodes.

In another aspect, a device for detecting electrographic seizure onset in a patient's brain is provided, the device comprising: two or more bipolar electrodes implantable into two or more separate regions of the hippocampi; an amplifier for amplifying said sensed icEEG of said regions; a digitizer for converting sensed icEEG recordings to digital data, and a processor for processing the digital data to detect said phase desynchronization between the two regions.

These and other aspects are contemplated and described herein. It will be appreciated that the foregoing summary sets out representative aspects of a system, method and apparatus for rapid brief feedback intracerebral stimulation based on real-time desynchronization to assist skilled readers in understanding the following detailed description.

DESCRIPTION OF THE DRAWINGS

A greater understanding of the embodiments will be had with reference to the Figures, in which.

DETAILED DESCRIPTION

Figure 1:
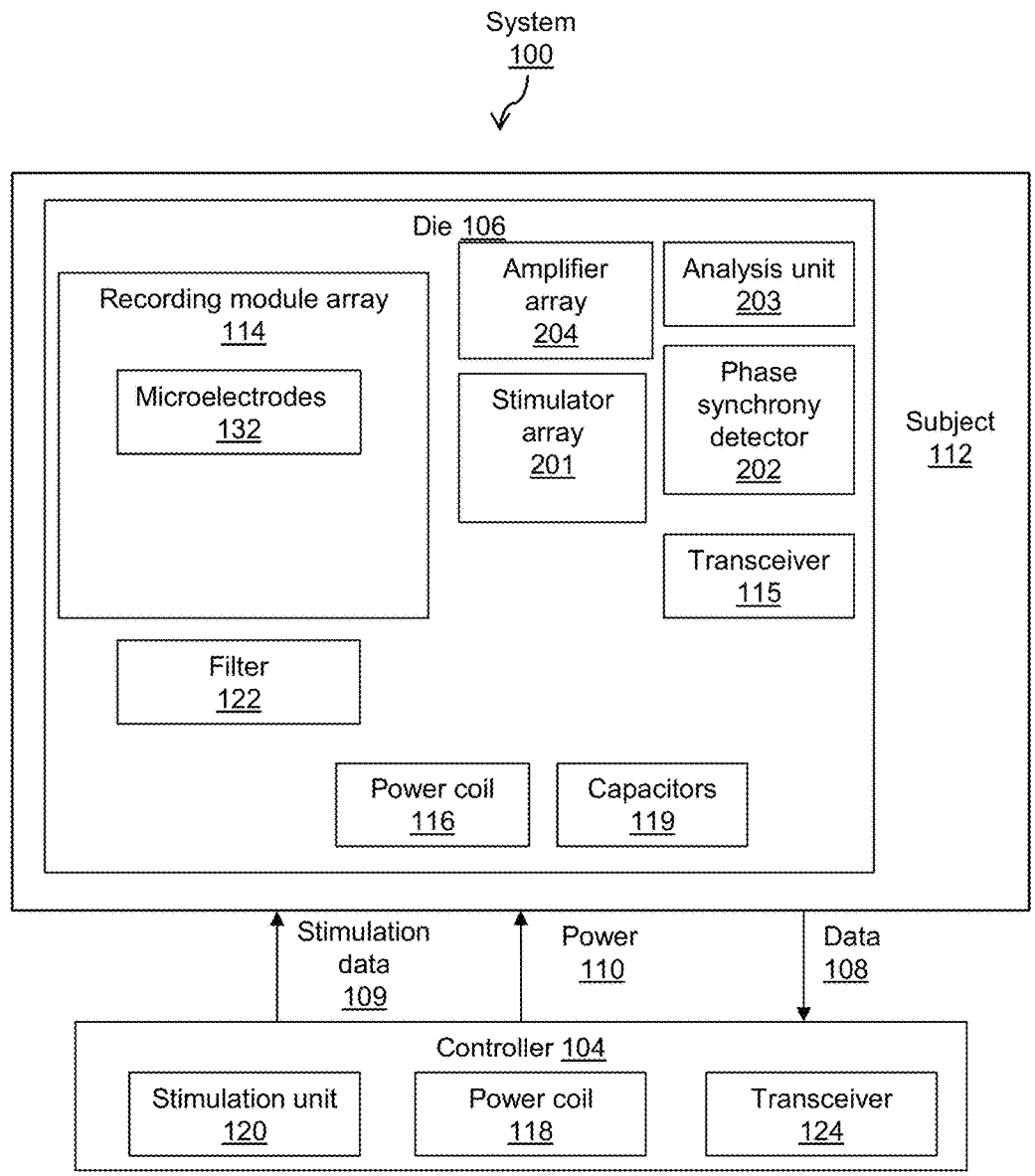
FIG. 1 shows a block diagram of an embodiment of a system for rapid brief feedback intracerebral stimulation.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Embodiments described herein generally provide a system, method and apparatus for monitoring and detecting abnormal patterns of synchrony in brain signals to, before the full paroxysm develops, stimulate and perturb the incipient abnormal synchrony patterns that could later result in a full-blown seizure. Applicant has determined that feedback stimulation at low frequencies for a few seconds after the detection of a seizure precursor can stop the development of paroxysms. Phase synchrony as a precursor detection has a myriad of possible advantages, including accuracy and the detection performance is less affected by changes in the recordings over time. An early relatively mild stimulation, before the full paroxysm develops, can perturb the incipient abnormal synchrony patterns that will later result in the full-blown seizure, whereas after the seizure has started stimulations of greater strengths may be required due to the robust high synchrony normally associated with seizures. The method can be implemented in real time in a computer or an implantable or wearable microchip. More specifically, embodiments implement a feedback perturbation to alter/stop abnormal brain patterns of synchrony and normalize the cellular collective activity using current stimulators, phase synchrony detection, neural recording amplifiers, real-time intracerebral recordings and signal analysis.

The somewhat limited success in the pharmacologic treatment of epileptic syndromes has aroused an increasing interest in the possibility of stopping seizures with brief direct electrical intracerebral stimulation. Support for the possible success of electrical perturbations in preventing seizures is based on the assumption that if the dynamics of the abnormal synchrony that characterizes paroxysms is perturbed by stimulations, then the ictus may not appear, or will be forced to stop if already initiated. Thus, the implementation of "minimal" (short duration, low frequencies and intensities) perturbations to stop the transition from the electrical activity to the ictal, convulsive event by a precisely timed brief stimulation has been a sort of "dynamic dream" in this field. Contrary to the current deep brain or vagus nerve stimulation paradigms that use intermittent (continuous) stimulation, the present system stimulates when a paroxysm is about to occur, using an on-demand feedback stimulation method based on real-time analysis of brain signals that detects a precursor of paroxysms, and implements a brief (e.g., 5 s) stimuli to stop the transition to the ictal event. Generally, an abnormal oscillation originates from an epileptogenic zone (often in hippocampus in temporal lobe epilepsy), which may disrupt theta wave (and others) synchronization with the other hippocampus. Over time, this focal oscillation spreads and often propagates contralaterally and develops a paroxysmal discharge. A feedback stimulator could disrupt the local epileptic oscillation and abort the seizure development.

The following terminology is used in the present disclosure. "Paroxysms" are any abnormal electrographic activities (e.g., duration≥10 s) associated with relatively high frequency and amplitude of spikes. When no apparent behavioral alterations are observed at the time of an electrographic paroxysm, the term "nonconvulsive paroxysm" is used, whereas the expression "convulsive paroxysm" is used if an abnormal behavior is observed concomitant with abnormal electrographic recording. The "paroxysm onset" is defined as the time when the amplitude of the electrographic recording in the paroxysm becomes greater than twice the standard deviation of the baseline activity. The "early paroxysm detection time" is the time between the detection of the seizure precursor and the paroxysm onset. The "preictal period" is defined as 1 minute before the paroxysm onset, and the "interictal period" is the time between the end of one paroxysm and the preictal of the next. The convulsive paroxysms are defined according to the Racine scale (class III to class IV), whereas the nonconvulsive paroxysms are class I or class II seizures.

Referring now to FIG. 1, shown therein is a block diagram of an embodiment of a system 100 for seizure precursor detection using rapid brief feedback intracerebral stimulation based on real-time desynchronization. The system 100 comprises an implantable or wearable die 106. The die 106 comprises a recording module array 114 and a stimulator array 201. The recording module array 114 is linked through an amplifier array 204 to the subject 112 and is configured to monitor and record signals of the subject's hippocampi. The stimulator array 201 is configured to deliver a current to the hippocampi. The die 106 further comprises a phase synchrony detector 202 and real-time intracerebral recordings and signal analysis unit 203.

The die may be powered by an external controller. In an example, an external stimulator controller 104 may serve as a power source to the die 106 through an inductive power coil 118 on the stimulator 104 and a mated inductive power coil 116 on the die 106.

More specifically, an embodiment of the die 106 is a millimetre size package-free complementary metal-oxide-semiconductor ("CMOS") chip (referred to below as "die") for obtaining real-time intracranial EEG measurements from the subject. The term "in situ" includes disposing the integrated circuit or an electrode coupled to the integrated circuit on, in or adjacent to a target region of the subject such that EEG measurements can be obtained from the target region.

The recording module array 114 comprises EEG recording microelectrodes 132. The die comprises a transceiver 115 for transmitting to the controller 114 data relating to the sensor readings, a power coil 116 for receiving energy by magnetic induction from the controller 104, and a bank of capacitors 119 for storing energy on the die to power the electronics of the die 106. More particularly, die 106 may be covered along a surface thereof with amperometric recording microelectrodes 132 when the die is positioned at a location of interest of a subject 112, in situ, and activated.

The controller 104 comprises a transceiver 124 and a power coil 118.

In the embodiment illustrated in FIG. 1, the die 106 may transmit data comprising recorded signals (illustrated as block 108) to the controller 104, and receives power therefrom (illustrated as block 110). Similarly, controller 104 transmits stimulation data back to the die 106, as illustrated by block 109. The die 106 may alternatively be linked by wire with the controller 104 or the controller 104 may be integrated on the die 106 or located on a chip adjacent the die 106.

In use, two bipolar electrodes 132 may be bilaterally implanted chronically into CA1 regions of both hippocampi of the subject 112, for example by using a stereotaxic micromanipulator. For an acute condition, a bipolar electrode 132 with a microcannula may be implanted similarly into the right CA1 region and another bipolar electrode 132 may be implanted into the left CA1 region. The electrodes 132 may be fixed to the skull using dental acrylic. The coordinates of electrode implantation may, for example, be: bregma −4.3, midline±3.0, depth 3.1.

The stimulator control 104 comprises a stimulation unit 120 that incorporates a processor. The stimulation unit 120 receives phase synchrony data from the die 106 as recorded by the recording electrode array 114, and transmits back to the die 106 a stimulation instruction to be carried out via the stimulator array 201. The stimulator unit 120 may further provide configuration instructions for the die for configuring recording instructions for the recording module array 114.

In a commercial embodiment, the stimulation unit may be implemented by a programmable feedback stimulator as described in Bagheri A, Gabran S R, Salam M T, et al. "Massively-parallel neuromonitoring and neurostimulation rodent headset with nanotextured flexible microelectrodes", IEEE Trans Biomed Circuits Syst 2013; 7:601-609, which is incorporated herein by reference.

The recording array 114 may be configured to acquire signals at 625 Hz and the stimulator array 201 may be configured to stimulate the subject 112 at 10 kHz. An exemplary feedback stimulator array 201, as an example, has 256 recording channels, 64 stimulation channels, and a built-in signal processor as described in Bagheri A, Gabran S R, Salam M T, et al. Massively-parallel neuromonitoring and neurostimulation rodent headset with nanotextured flexible microelectrodes. IEEE Trans Biomed Circuits Syst 2013; 7:601-609, which is incorporated herein by reference. In this implementation, the amplifier array 204 for the recording channels has a mid-band gain programmable from 54 dB to 72 dB, programmable bandwidth of 0.1 Hz to 5 kHz with 7.99 μVrms input-referred noise. The amplifier array 204 may comprise a digitizer to digitize the signals.

The intracerebral bipolar recordings from both hippocampi may be recorded by the recording module array 114 and sent to the controller 104 for real-time phase synchrony analysis using, for example, Matlab-based custom-made algorithms. Initially, the recordings may be band-pass filtered by filter 122 with cutoff frequencies of F±2 Hz, where F is a central frequency. Interesting central frequencies are 5 Hz, 8 Hz, 15 Hz and 25 Hz. The phase synchrony may be investigated at central frequency of 8 Hz and the phase synchrony index values may be averaged throughout a 1 s time window. The phase synchrony index may be defined as $R=|\langle e^{i\Delta\theta}\rangle|$, where ei is the exponential integral and $\Delta\theta$ is the phase difference between the two hippocampal recordings.

The feedback electrical stimulation may comprise a burst of square-wave current pulses bipolar biphasic current pulses of 150 μA, pulse width 100 μs, frequency 5 Hz, and duration 5 s triggered by the real-time synchrony analysis 202 on response to the seizure precursor detection. The stimulation may be delivered to the right or left hippocampus (depending on seizure initiation). The stimulation current may be chosen according to safety considerations, which may be three times lower than the maximum deliverable charge per phase.

Figure 8:
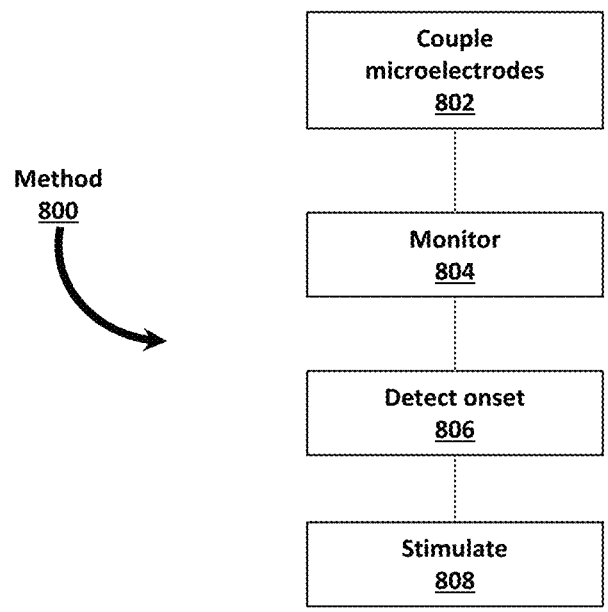
FIG. 8 shows a method for rapid brief feedback intracerebral stimulation.

FIG. 8 illustrates a method 800 enabled by the system shown in FIG. 1. At block 802, intracranial EEG (icEEG) microelectrodes are coupled to two hippocampi of the patient. At block 804, the microelectrodes are continuously monitored. The monitoring may comprise identifying phase desynchronization at theta wave in between said hippocampi icEEG recordings at seizure onset. Further, the monitored (or sensed) icEEG of the hippocampi may be amplified to obtain amplified icEEG recordings, and the amplified signals then digitalized to obtain the digital data, so that the digital data can be used with a seizure onset detection algorithm to trigger a current stimulator for said stimulation of said hippocampus. The signals may further be filtered with cutoff frequencies of cental frequency±2 Hz. The central frequency may be 5 Hz, 8 Hz, 15 Hz and 25 Hz.

At block 806, the stimulation unit detects seizure onset using phase synchronization analysis. A phase synchrony index is determined at the cutoff frequencies, where said phase synchrony index is defined as $R=|\langle e^{i\Delta\theta}\rangle|$, where $\Delta\theta$ is the phase difference between the said hippocampi recordings. The phase synchrony index values may be averaged throughout a 1 sec time window.

At block 808, the stimulation unit stimulates the hippocampus (seizure origination) of the patient upon detection of a seizure onset by the sensed icEEG of the hippocampi. The stimulation parameters may be a 5-second train of 5 Hz stimulus pulses. Stimulating with these parameters may restore theta wave synchronization in between the hippocampi during the phase desynchronization at theta wave at seizure onset.

Stimulating may comprise implanting two bipolar microelectrodes (each bipolar microelectrode comprises assembling of two insulated microwires and exposed tip of the wire uses for icEEG recoding; diameter of the exposed region: 100 μm and interspacing between two wires: 25 μm) into CA regions of the hippocampi, and passing current stimulation pulses between two contacts of the bipolar microelectrode through tissue of the hippocampus.

Figure 2:
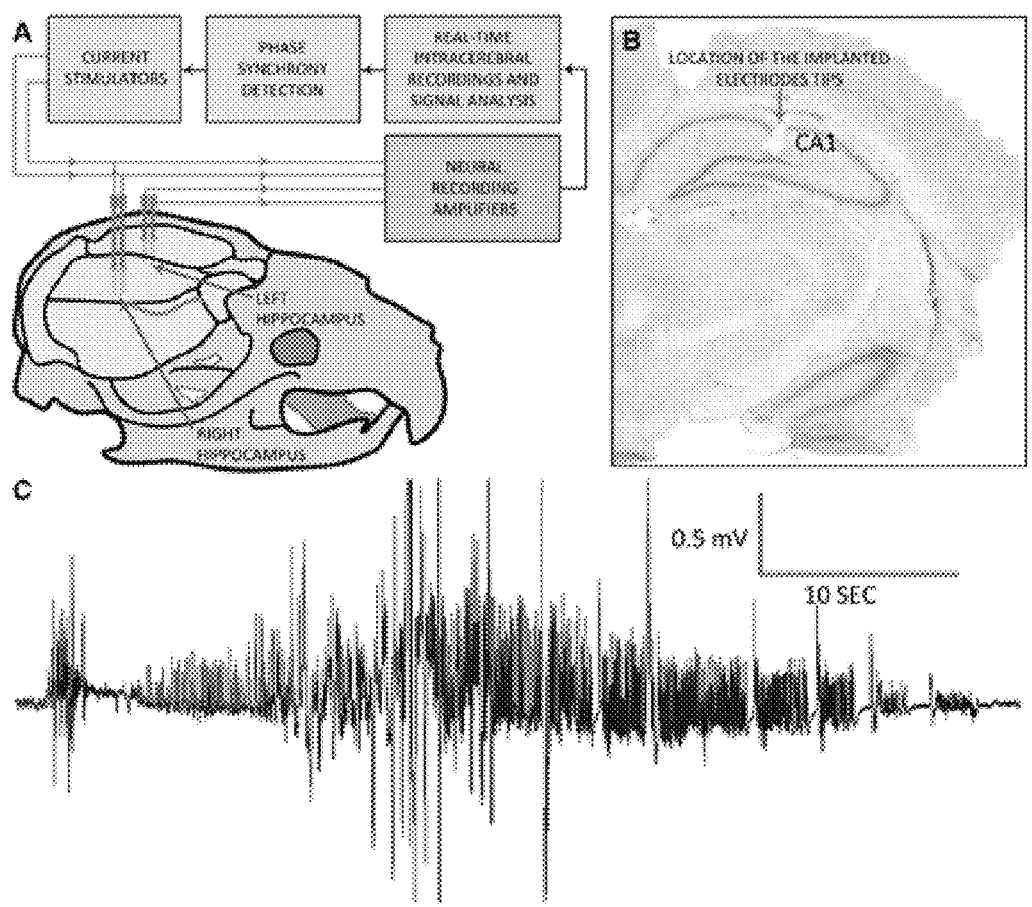
FIG. 2 shows application of the system in a rat and a representative example of a spontaneous paroxysm in the chronic condition.

Referring now to FIG. 2, an example implementation of the system is shown. FIG. 2(a) shows a general scheme of the system having current stimulators, phase synchrony detection, real-time intracerebral recordings and signal analysis, and neural recording amplifiers. FIG. 2(b) shows a cresyl-violet stained brain section showing the location of the implanted electrode tips. FIG. 2(c) shows a representative example of a spontaneous paroxysm in the chronic condition.

An example experiment conducted on rats using the above system will now be described. Two well-characterized rodent seizure models were used to reproduce some features of human temporal lobe epilepsy. The seizure induction procedures of the two models are described below.

Chronic condition: Kainic acid (KA, 13 mg/kg dissolved in saline) was injected intraperitoneally into 46 Wistar rats to induce temporal lobe paroxysms. One month to 2 months after the injection, recurrent spontaneous convulsive and nonconvulsive paroxysms developed in 11 rats, which were used for the chronic condition experiments.

Acute condition: 4-AP (300-500 nmol, 6-8 µl) was injected in 12 rats through an implanted cannula into the right hippocampus. Following the injection, eight rats had spontaneous recurrent electrographic seizures for at least 2 h and were used in the experiments.

All rats with seizures were divided randomly into two groups: (1) nonstimulation group and (2) stimulation group. In the nonstimulation group (five rats in the chronic experiment and four in the acute experiment), seizures were monitored and marked, and the seizure frequency per hour was determined. The stimulation group went through four experimental phases for the evaluation of the efficacy of the feedback stimulation: phase I, no stimulation; phase II, feedback stimulation; phase III, no stimulation; and phase IV, open-loop stimulation. Each of the phases was 6 days long. In phase I, seizures were monitored and marked; subsequently, in phase-II, the feedback stimulator was turned on to trigger the electrical stimulation upon an electrographic seizure precursor detection. The number of feedback stimulations per day in the stimulation group was quantified and used in phase IV. Then, in phase III, the feedback stimulation was turned off. Next, in phase IV, an open-loop stimulation paradigm was implemented using the same average number of stimulations per day as in phase II, but in a periodic manner (equal intervals), thus not associated with the detection of the seizure precursor. This phase served as a control for the specificity of the feedback stimulation. During these four phases, all paroxysms were monitored, classified, and the frequency per day determined.

The following statistical measures were used to assess the paroxysm detection performance.

True positives (TP): the number of paroxysms that followed the detection of the putative seizure precursor—a decrease in the phase synchronization index.

False positives (FP) or false alarm: when a paroxysm does not follow the detection of the seizure precursor.

True negatives: nonparoxysmal activity correctly identified as nonparoxysmal.

False negatives (FN): the paroxysms that occurred without the detection of the seizure precursor.

Sensitivity: the ratio of the number of TP to the total number of TP and FN.

Specificity: the ratio of the number of true negatives to the total number of TN and FP.

Statistical tests were performed in Matlab using the Statistics Toolbox. Results are expressed as mean ± standard deviation (STD). Statistical significance of differences in synchrony indices and spectral power during interictal, preictal and paroxysm periods, and paroxysm rate differences between baseline, open-loop stimulation, and closed-loop stimulation periods, were evaluated using a one-way repeated-measure analysis of variance (ANOVA). A Fisher's least significant difference (LSD) test was used to determine the significance between the various group means. The level of significance was set to $p<0.05$.

Figure 3:
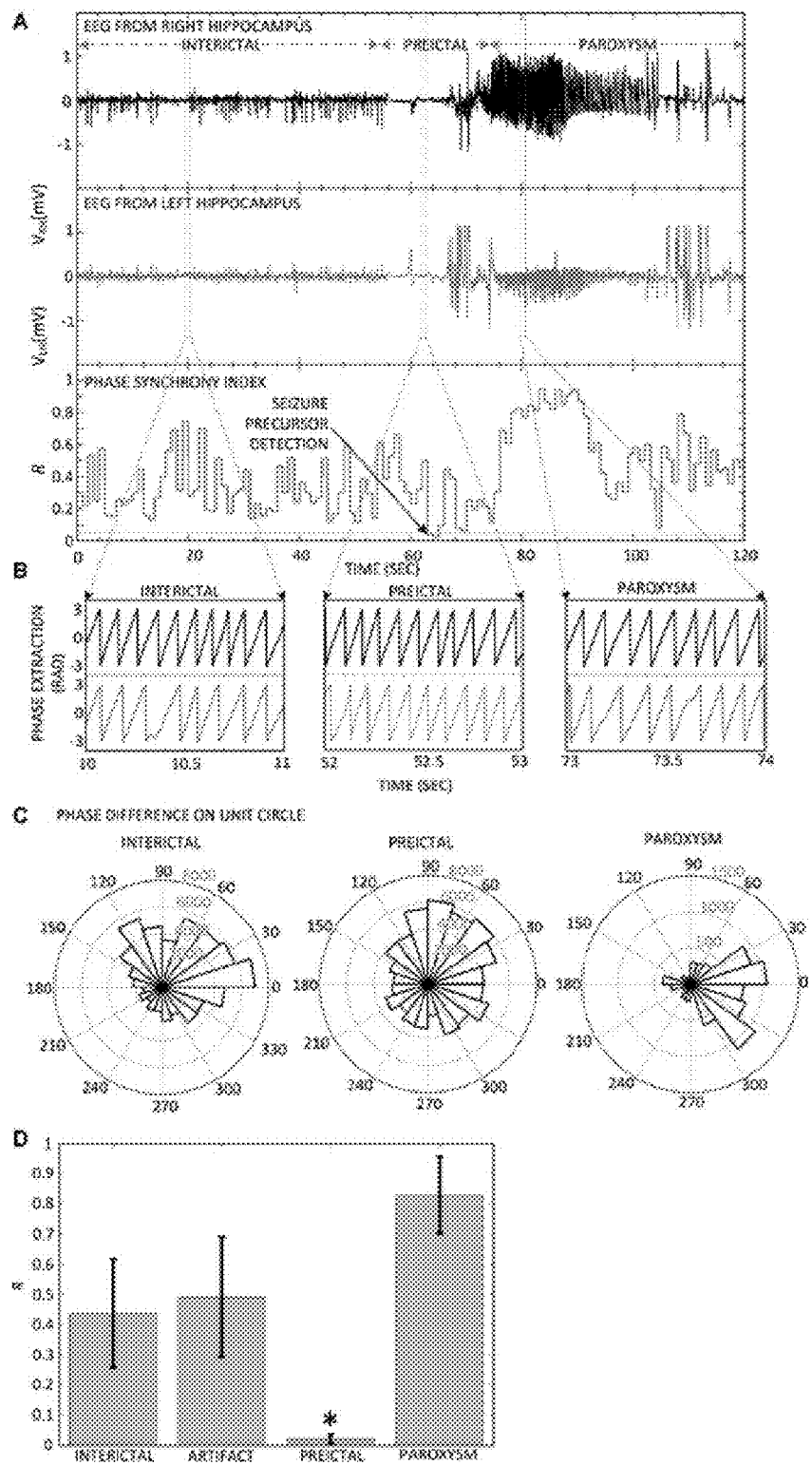
FIG. 3 shows example data of seizure precursor detection performance of the system in the chronic condition.

Referring now to FIG. 3, shown therein is an example embodiment of seizure precursor detection performance in the chronic condition. More specifically, the example embodiment shown in FIG. 3 illustrates the recordings from the right and left hippocampus and the evolution of the R index in the third row. Its value fluctuates between 0.2 to 0.7 during the interictal period; however, it drops below 0.1 during the preictal period, and gradually increases subsequently above 0.8 during the paroxysm. The phase desynchronization ($R<0.1$) was observed before the paroxysm onset in all rats (n=19) in both the chronic and acute conditions.

FIG. 3(a) shows an example of the precursor detection (a value of the R synchrony index, evaluated at central frequency of 8 Hz, below the threshold of 0.05 marked by the solid arrow) for a rat of the non-stimulation group. Upper traces are the recordings from both hippocampi showing the paroxysm approximately from the time period 70-100 s; the lower graph is the time evolution of the R index. The high synchrony (R) value is noticed during most of the paroxysm; the paroxysm detection threshold of FIG. 3(a) was consistent for the all animals; therefore, no optimization was required. This threshold was used in the feedback system to trigger a stimulation. FIG. 3(b) shows phase (wrapped) extraction from interictal, preictal, and ictal periods in both hippocampal signals used to compute the synchrony index. The typical sawtooth shape (extracted phase) can be seen in all three segments, indicating that the algorithm was able to extract the phases regardless of signal amplitude as the signals during the paroxysm have higher amplitudes; FIG. 3(c) shows phase differences on the unit circle, where it can be seen the more dispersed distribution of angles during the preictal state translates into a lower R index; FIG. 3(d) shows the averages of the evolution of the phase synchrony index R between two hemispheres during interictal, artifact, preictal, and paroxysmal periods. The magnitude of R drops significantly during the preictal period (*$p<0.05$ for preictal vs interictal, artifact or paroxysm periods). "Artifact" denotes the times when the rat was moving (the moving artifacts were marked using the video recordings).

In the chronic condition, the paroxysm detection performance was evaluated online and offline (reevaluated) in the nonstimulation group and during the no-stimulation phases of the stimulation group.

Figure 4:
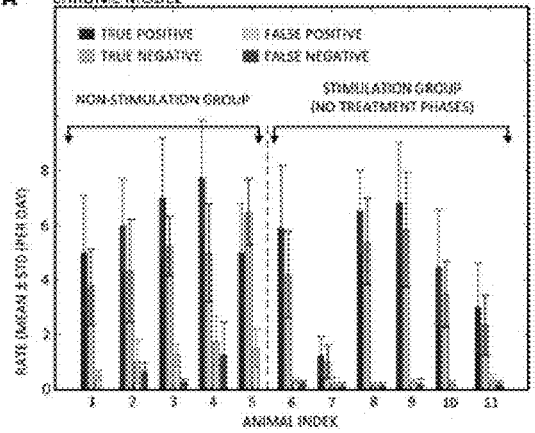
FIG. 4 shows example data of detection performance of the system in the chronic and acute conditions.
Figure 4:
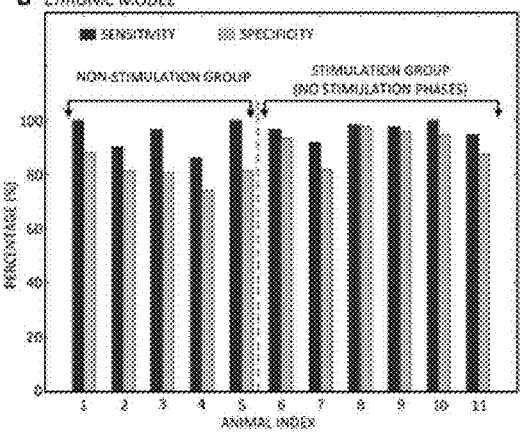
Figure 4:
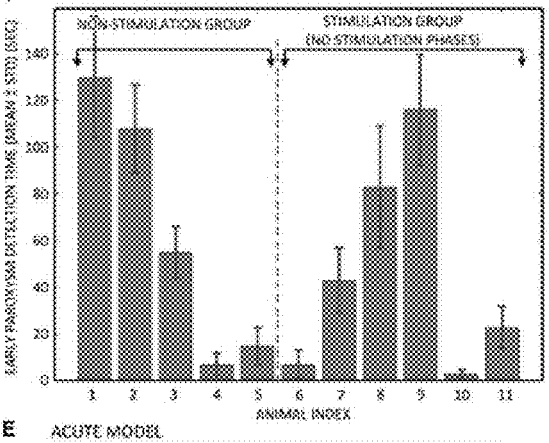
Figure 4:
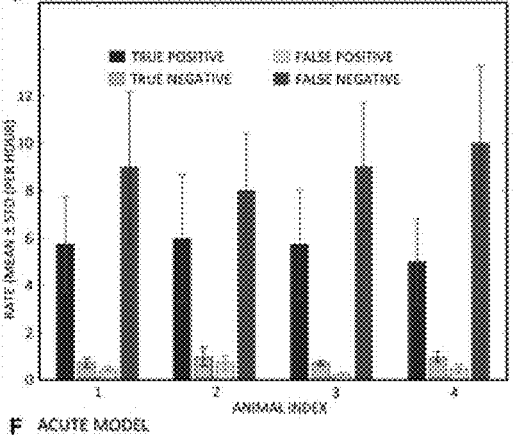
Figure 4:
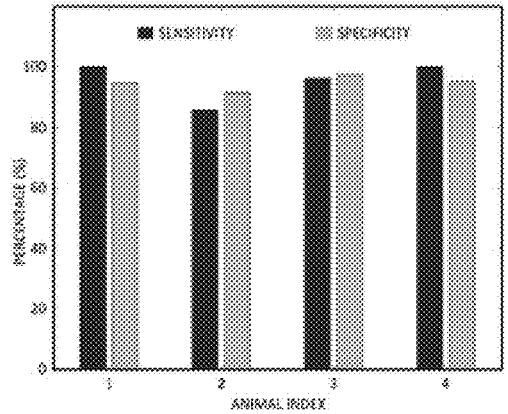
Figure 4:
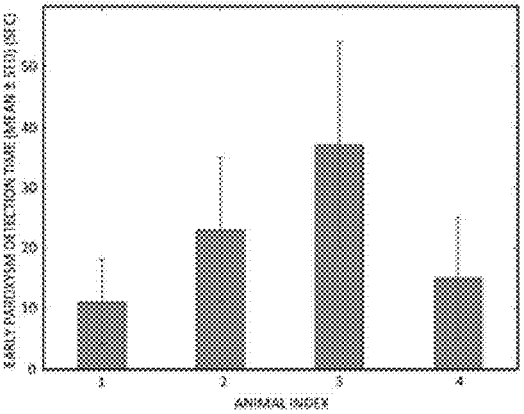

Referring now to FIG. 4, shown therein is an example embodiment of detection performance of the seizure precursor in the chronic and acute conditions. FIG. 4(a) and FIG. 4(b) show seizure-onset detection performance based on 494 seizures from the nonstimulation group (five rats) and no-stimulation periods of the stimulation group (six rats); FIG. 4(c) shows early paroxysm detection times for both groups: the time when the minimum in the phase synchrony index was detected before seizure onset; FIG. 4(d) and FIG. 4(e) show seizure-onset detection performance based on 104 paroxysms from the nonstimulation group in the acute condition (four rats); FIG. 4(f) shows the time before seizure onset when the minimum of the R synchrony index was detected.

More specifically, the example embodiment shown in FIG. 4(a) through FIG. 4(c) illustrates the detection performance where the phase synchronization analysis detected 95% (351 of 369) of the convulsive paroxysms and 66% (83 of 125) of the non-convulsive paroxysms, with 0.67±0.59 false alarms per day. The overall sensitivity and specificity of the detection were 88% and 86%, respectively. The average early paroxysm detection time was 53.64±13.64 s. In the acute condition shown in FIG. 4(d) through FIG. 4(f), the paroxysm detection performance was similarly evaluated online and offline in the nonstimulation group. The phase synchronization analysis detected 90% (27 of 30) of the convulsive paroxysms and 79% (59 of 74) of nonconvulsive paroxysms. The overall sensitivity and specificity of the detection were 84% and 94%, respectively; with 0.47±0.20 false alarms per hour. The average early paroxysm detection time was 21.50±11.50 s.

Figure 5:
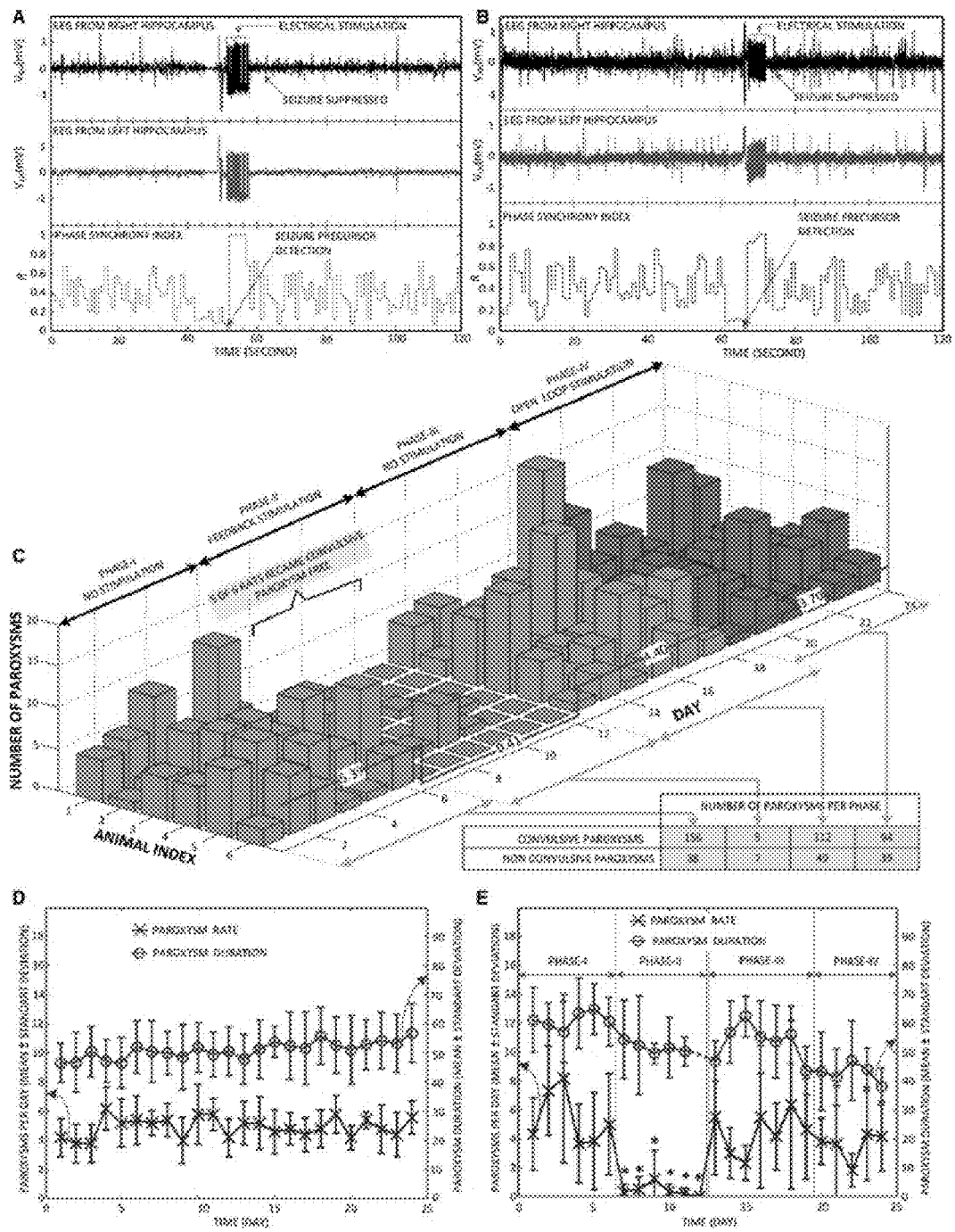
FIG. 5 shows example data of seizure suppression of the system.

Referring now to FIG. 5, shown therein are representative examples of seizure suppression by the feedback electrical stimulation for a rat in the stimulation group of chronic (a) and acute (b) models. In the chronic condition, the seizure frequency in the stimulation group was ~5.39 paroxysms per day in phase I (no-stimulation baseline). In phase II, the feedback stimulation delivered to the hippocampus after the detection of the precursor (FIG. 5(a)) resulted in five of the six rats in the stimulation group becoming convulsive paroxysm free, and a 93% reduction of seizure frequency in the sixth rat. Following the feedback stimulation phase, the rats underwent a no-stimulation phase III, which resulted in the average seizure rate going back to that of phase I (FIG. 5(c) through FIG. 5(e)). In phase IV, an open-loop stimulation was delivered. The open loop stimulation reduced the paroxysm frequencies found in phase I and phase III by 32% and 19%, respectively (FIG. 5(c) through FIG. 5(e)). Thus, the example embodiment illustrates that the feedback stimulation significantly reduced paroxysmal activity due to the precise timing of stimulation triggered by the seizure precursor detector.

More specifically, the example embodiment shown in FIG. 5 illustrates after the R index falls below the predefined threshold (denoted by the discontinuous line in third row), the feedback system triggers the stimuli and no paroxysmal event follows, and there is no increase in the synchrony characteristic of seizures (see also FIG. 3(a), third row). The high value of the synchrony index (R in third rows of FIG. 5(a) and FIG. 5(b)) was due to the 5 s stimulation artifact; (c) shows seizure suppression results in the chronic condition. During the 6 days of the no-stimulation phase I, ~5.39 seizures per day on average were observed. The stimulation phase II reduced seizure rate to 0.41, and afterwards, another no-stimulation phase (phase III) yielded ~4.40 seizures per day. The final phase, open-loop stimulation, presented on average 3.70 seizures per day. The table/inset indicates number of convulsive and nonconvulsive paroxysms. Statistical analysis of paroxysm frequency (black line) and paroxysm duration (red line) of the chronic experiment in nonstimulation (d) and stimulation (e) groups. The feedback stimulation phase had reduced 91.68% and 89% paroxysm frequencies compared to the nonstimulation group and no-stimulation phases of stimulation group, respectively (*p<0.05 for feedback stimulation vs. no-stimulation phases and nonstimulation group).

Figure 6:
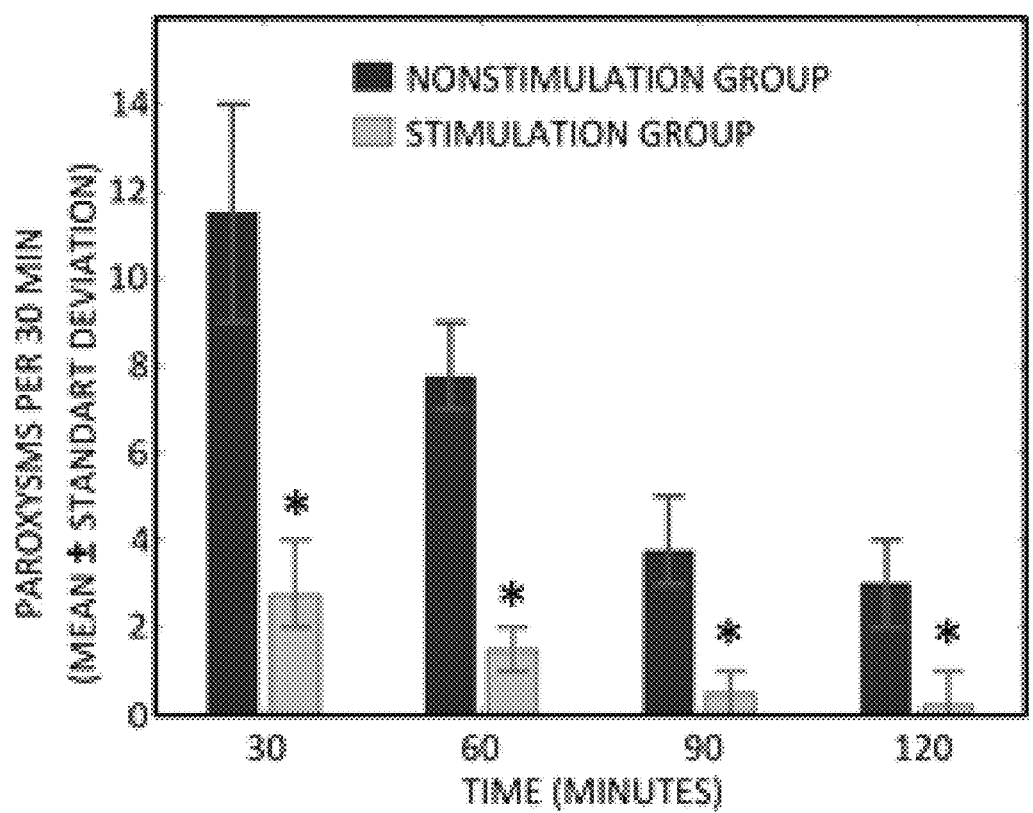
FIG. 6 shows example data of seizure suppression of the system.

Referring now to FIG. 6, shown therein is an example embodiment of seizure suppression results in the acute condition. In the acute condition, the average number of paroxysms in the nonstimulation group was quantified in 30 min periods. The stimulation group, which received the feedback stimulation right after the detection of the seizure precursor, had a reduced 81% paroxysm frequency compared to the nonstimulation group (p<0.05). The stimulation group had a reduced 89% paroxysm frequency compared to the nonstimulation group (*p<0.05 for stimulation vs nonstimulation groups).

Figure 7:
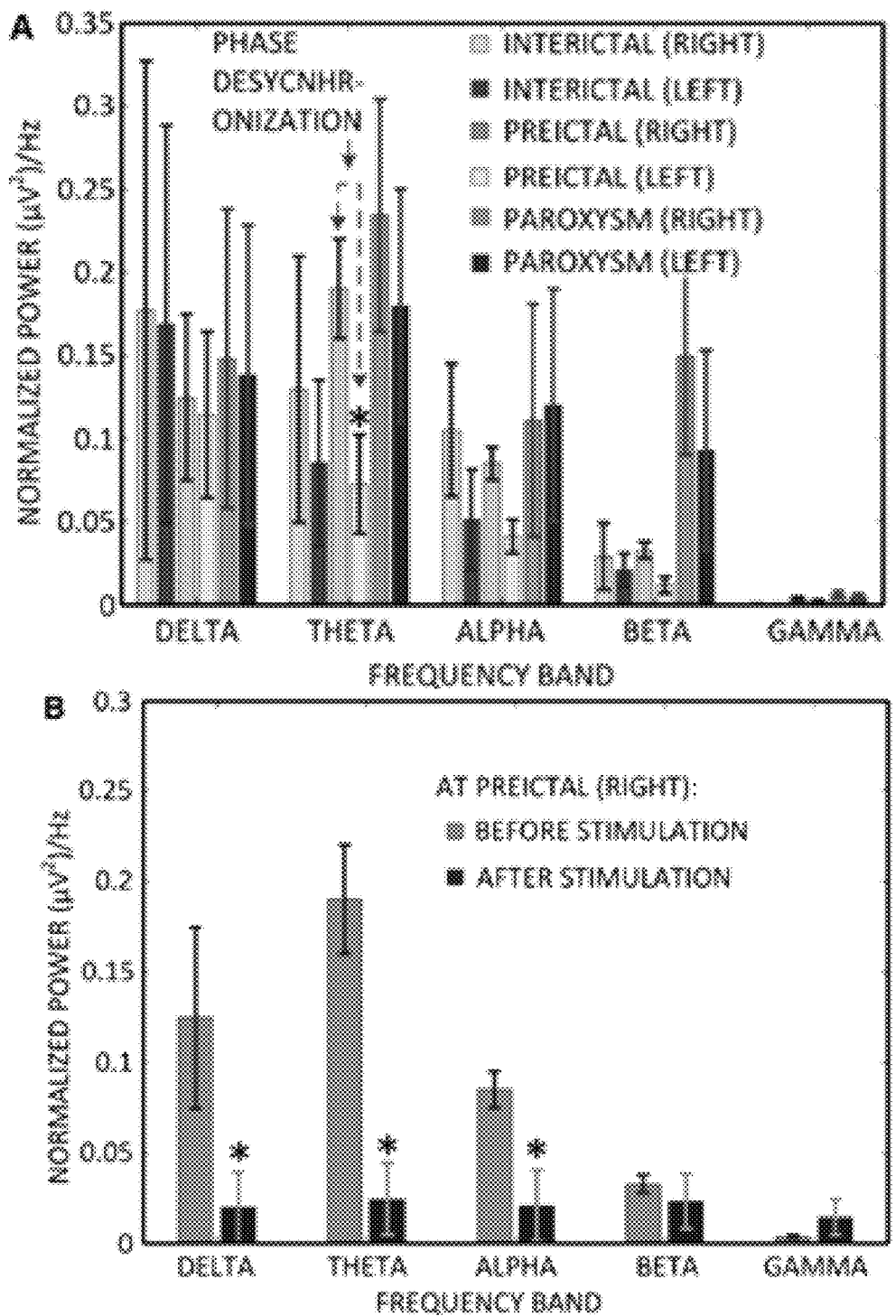
FIG. 7 shows example spectral analysis of power levels in different frequency bands for the system.

Referring now to FIG. 7, shown therein is an example embodiment of spectral analysis. (a) shows mean power spectra (±STD) of the intracerebral recordings from the right hippocampus and left hippocampus during interictal, preictal, and paroxysm periods. More specifically, there was a statistically significant divergence in power between both hemisphere signals during the preictal period at the theta band indicated in the figure (*p<0.05 for right vs. left sides), whereas during the interictal and ictal times, the power fluctuates in a coordinated manner. These phenomena will be reflected in a decrease in phase synchrony during the preictal time. (b) shows mean power spectrum (±STD) analysis before and after feedback stimulation during the preictal time. It is shown that the power in the lower frequency bands diminishes as compared to that just before the stimulation, more prominently at theta frequencies (80% reduction in theta power; *p<0.05 for "after" vs. "before" stimulation).

The possible mechanisms for the seizure precursor will now be discussed in detail with reference to FIG. 3, FIG. 5 and FIG. 7.

The decrease in synchrony prior to a paroxysm (FIG. 3(a)) may be caused by the different activities in the localized neighboring cells. If each neighborhood starts to fire spikes at different frequencies (yet synchronously within that neighborhood), then it is conceivable that two relatively distant regions will have different neighborhoods firing at distinct frequencies thus the decrease in phase locking between the two hippocampal signals is expected. This scenario is supported by the spectral analysis shown in FIG. 6(a). Power levels in different frequency bands were changing almost simultaneously in the right and left signals during the interictal and ictal periods; however, during the preictal period, there were apparent divergences in power between both recordings, and this occurred in 87% (520 of 598) of the preictal stages evaluated.

In particular, the θ band power had a sharper difference between the two signals. Thus, as a consequence of this divergence in oscillatory power, a phase desynchronization between both hippocampi is expected to occur at the preictal period prior to the paroxysm onset (as shown in FIG. 3(a) and FIG. 5(a)). The divergence in power was seen as well in other frequency bands; however, it was more abundant and pronounced in the θ band: it occurred in 71% (370 of 520) with>50% increase from baseline at θ, 56% (292 of 520) with>23% increase from baseline at β, 35% (183 of 520) with>52% increase from baseline at α, 48% (250 of 520) with>52% increase from baseline at δ, whereas the γ band was relatively unaffected (4%, 21 of 520). The power differences at all bands between both recordings were not statistically different during the paroxysmal period (FIG. 7(a)).

The effects of the feedback stimulation will now be discussed in detail with reference to FIG. 3, FIG. 5 and FIG. 7.

To investigate possible reasons of the success of the feedback stimulation, similar power spectral analysis after the stimuli was carried out, and as well, the temporal evolution of the phase synchrony index after the stimuli as compared to the synchrony when no stimulation was implemented (and thus paroxysms developed) was assessed. The exemplary embodiment of FIG. 7(b) indicates that the net effect after the stimulation was a decrease in power at low frequencies with no apparent changes at higher bands (β and γ). The decreased power relative to that during the normal development of the paroxysm was 56%, 80%, and 40% of the δ, θ, and α bands, respectively. The power remained at the reduced levels for 2-3 s following the feedback stimuli and later gradually recovered back to the interictal level. Regarding the temporal evolution of the phase synchrony index), the typical increase in synchrony during the paroxysm was observed (FIG. 3(a)), but after a successful stimulation (in that there was no paroxysmal discharge right after) (FIG. 5(a) and FIG. 5(b)), the synchrony values did not change significantly from those values during the baseline, interictal periods. Hence, the combined results of the spectral and the synchrony analyses indicate that the stimulus upon the detection of the desynchronization just before a possible seizure effectively prevents the progress of the abnormal pattern of synchrony (mainly at δ, θ, and α bands) between the two hippocampi that develops into a paroxysm.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A method of monitoring, detecting and stimulating a human patient with epilepsy, said method comprising:
    monitoring said patient for a seizure onset by intracranial EEG (icEEG) microelectrodes coupled to two hippocampi of the patient to obtain icEEG recordings in real time;
    detecting said seizure onset using phase synchronization analysis, the phase synchronization analysis identifying phase desynchronization at theta wave in between the two hippocampi from said icEEG recordings at seizure onset; and
    stimulating one of the two hippocampi of the patient upon detection of a seizure onset by said icEEG recordings of said two hippocampi to restore theta wave synchronization in between the two hippocampi.

2. The method of claim 1 further comprising:
    amplifying said icEEG recordings of said two hippocampi to obtain amplified icEEG recordings;
    digitalizing said amplified icEEG recordings to obtain digital data;
    using said digital data and said seizure onset detection to trigger a current stimulator for said stimulation of one of the two hippocampi of the patient.

3. The method of claim 2 wherein phase synchronization analysis comprises:
    filtering said amplified icEEG recordings with cutoff frequencies of central frequency±2 Hz to obtain filtered icEEG recordings;
    investigating phase synchrony index at said cutoff frequencies, where said phase synchrony index is defined as $R=|\langle e^{i\Delta\Theta}\rangle|$, where $\Delta\theta$ is the phase difference between said filtered icEEG recordings; and
    averaging said phase synchrony index values throughout a 1 sec time window.

4. The method of claim 3, wherein the central frequency is one of 5 Hz, 8 Hz, 15 Hz and 25 Hz.

5. The method of claim 1 wherein said stimulation of one of the two hippocampi of the patient is accomplished with stimulation parameters that include a 5-second pulse train of 5 Hz stimulus pulses.

6. The method of claim 5 wherein stimulating with said stimulation parameters restores said theta wave synchronization in between said two hippocampi during said phase desynchronization at theta wave at seizure onset.

7. The method of claim 1 wherein said stimulating comprises:
    implanting two bipolar microelectrodes into CA regions of each of said two hippocampi, each bipolar microelectrode comprising assembling of two insulated microwires, each insulated microwire having an exposed tip used for icEEG recording, wherein the diameter of the exposed tip is 100 μm and interspacing between the two insulated microwires is 25 μm; and
    passing current stimulation pulses between two contacts of each of said two bipolar microelectrodes through tissue of one of the two hippocampi.

8. The method of claim 1 wherein said monitoring comprises:
    implanting two bipolar microelectrodes into CA regions of said two hippocampi, each bipolar microelectrode comprising assembling of two insulated microwires, each insulated microwire having an exposed tip used for icEEG recording, wherein the diameter of the exposed tip is 100 μm and interspacing between the two insulated microwires is 25 μm; and
    sensing icEEG of said two hippocampi with said two bipolar microelectrodes.

9. A device for detecting electrographic seizure onset in a patient's brain comprising:
    two or more bipolar electrodes configured to be implanted into two or more separate regions to obtain intracranial EEG (icEEG) recordings in real time, each region located in either one of the hippocampi of the patient's brain;
    an amplifier for amplifying said icEEG recordings of said two or more separate regions to obtain amplified icEEG recordings;
    a digitizer for converting said amplified icEEG recordings to digital data;
    a processor for processing the digital data to detect phase desynchronization at theta wave between the two or more separate regions to detect seizure onset; and
    a current stimulator for stimulating at least one of the two or more separate regions of the patient upon detection of a seizure onset by said icEEG recordings to restore theta wave synchronization between the two or more separate regions.

* * * * *